(12) United States Patent
Hsia et al.

(10) Patent No.: US 8,273,857 B2
(45) Date of Patent: Sep. 25, 2012

(54) COMPOSITIONS AND METHODS OF USE OF NEUROVASCULAR PROTECTIVE MULTIFUNCTIONAL POLYNITROXYLATED PEGYLATED CARBOXY HEMOGLOBINS FOR TRANSFUSION AND CRITICAL CARE MEDICINE

(76) Inventors: Jen-Chang Hsia, Laguna Woods, CA (US); Li Ma, Statesboro, GA (US)

( * ) Notice: Subject to any disclaimer, the term of this patent is extended or adjusted under 35 U.S.C. 154(b) by 38 days.

(21) Appl. No.: 12/924,246

(22) Filed: Sep. 22, 2010

(65) Prior Publication Data

US 2011/0071275 A1 Mar. 24, 2011

Related U.S. Application Data

(60) Provisional application No. 61/244,777, filed on Sep. 22, 2009.

(51) Int. Cl.
*A61K 35/14* (2006.01)
(52) U.S. Cl. ........................................ 530/385
(58) Field of Classification Search ............... 530/385
See application file for complete search history.

(56) References Cited

U.S. PATENT DOCUMENTS

| | | |
|---|---|---|
| 392,534 A | 12/1975 | Mazur |
| 400,120 A | 1/1977 | Bonsen et al. |
| 400,140 A | 1/1977 | Bonsen et al. |
| 405,359 A | 10/1977 | Bonsen et al. |
| 406,173 A | 12/1977 | Morris et al. |
| 413,609 A | 1/1979 | Bonhard et al. |
| 430,114 A | 11/1981 | Iwashita et al. |
| 433,624 A | 6/1982 | Bonhard et al. |
| 437,609 A | 3/1983 | Hasegawa |
| 437,751 A | 3/1983 | Ajisaka et al. |
| 440,165 A | 8/1983 | Simmonds et al. |
| 441,298 A | 11/1983 | Iwashita et al. |
| 447,349 A | 9/1984 | Tye |
| 452,971 A | 7/1985 | Tye |
| 456,334 A | 1/1986 | Miyata et al. |
| 458,413 A | 4/1986 | Bucci et al. |
| 459,806 A | 7/1986 | Walder |
| 460,053 A | 7/1986 | Walder |
| 467,041 A | 6/1987 | Iwasaki et al. |
| 482,681 A | 5/1989 | Sehgal et al. |
| 483,101 A | 5/1989 | Estep |
| 485,763 A | 8/1989 | Hsia |
| 486,371 A | 9/1989 | Keana |
| 491,192 A | 3/1990 | Farmer et al. |
| 492,019 A | 4/1990 | Feller et al. |
| 492,557 A | 5/1990 | Hsia |
| 505,135 A | 9/1991 | Stratton et al. |
| 506,168 A | 10/1991 | Beissinger et al. |
| 511,493 A | 5/1992 | Runge |
| 523,490 A | 8/1993 | Nho et al. |
| 559,171 A | 1/1997 | Hsia |
| 560,602 A | 2/1997 | D'Agnillo |
| 572,583 A | 3/1998 | Hsia |
| 578,937 A | 8/1998 | Hsia |
| 584,070 A | 11/1998 | Hsia |
| 584,085 A | 11/1998 | Rausch et al. |
| 604,896 A | 4/2000 | Hsia |
| 6,197,745 B1 | 3/2001 | Stamler |
| 6,323,175 B1 | 11/2001 | Hsia |
| 6,458,758 B1 | 10/2002 | Hsia |
| 6,627,738 B2 | 9/2003 | Stamler |
| 6,747,132 B2 | 6/2004 | Privalle et al. |
| 6,844,317 B2 | 1/2005 | Winslow et al. |
| 6,884,773 B1 | 4/2005 | Stamler |
| 6,911,427 B1 | 6/2005 | Stamler |
| 6,974,795 B2 | 12/2005 | Winslow et al. |
| 7,135,553 B2 | 11/2006 | Avella et al. |
| 7,144,989 B2 | 12/2006 | Acharya et al. |
| 7,169,900 B2 | 1/2007 | Acharya et al. |
| 7,411,044 B2 | 8/2008 | Avella et al. |
| 7,776,526 B2 | 8/2010 | Zal et al. |
| 2003/0181358 A1 | 9/2003 | Zal et al. |
| 2006/0182815 A1 | 8/2006 | Gladwin et al. |
| 2006/0234915 A1* | 10/2006 | Winslow ................. 514/6 |
| 2007/0154569 A1 | 7/2007 | Gladwin et al. |
| 2010/0051025 A1 | 3/2010 | Zapol et al. |

* cited by examiner

Primary Examiner — Suzanne M Noakes (57) ABSTRACT

The present invention describes neuroprotective and multi-functional intra- and inter-molecular redox coupled polynitroxylated pegylated carboxy hemoglobins as high therapeutic index agents for un-met medical needs or diseases, which require acute or chronic alleviation of oxidative stress and correction of inadequate blood flow resulting from physical injury, ischemia, reperfusion injury, and inflammation injury in either or both pre-hospital and in-hospital transfusion and critical care medicine. These hemoglobins are triple-modified with a focus on therapeutic activities rather than oxygen carrying ability.

15 Claims, 12 Drawing Sheets

Figure 12 ból# COMPOSITIONS AND METHODS OF USE OF NEUROVASCULAR PROTECTIVE MULTIFUNCTIONAL POLYNITROXYLATED PEGYLATED CARBOXY HEMOGLOBINS FOR TRANSFUSION AND CRITICAL CARE MEDICINE

CROSS-REFERENCE TO RELATED APPLICATIONS

This application claims the benefit of provisional patent application number 61/244,777 filed Sep. 22, 2009.

FEDERALLY SPONSORED RESEARCH

Nonapplicable

SEQUENCE LISTING OR PROGRAM

Nonapplicable

FIELD OF THE INVENTION

This invention relates to compositions and methods of use of novel neurovascular protective polynitroxylated pegylated carboxy hemoglobins as multifunctional hemoglobin based therapeutics primarily for use in transfusion and critical care medicine.

BACKGROUND

Prior Art

This invention relates generally to the composition and use of a heme iron redox coupled with nitroxide and shielded in a shell of hydrated biocompatible polymers (HNP), in a physiological solution for the treatment of oxidative stress and inadequate blood flow via superoxide dismutation, hydrogen peroxide breakdown and nitric oxide preservation rather than serving mainly as an oxygen carrier for use in the fields of pre-hospital and in-hospital transfusion and critical care medicine. The HNPs are to replace blood transfusion where blood is un-available in a pre-hospital setting or the blood transfusion is un-able to ameliorate or may even aggravate oxidative stress in an in-hospital setting. The HNP is a multifunctional therapeutic product, which is to be used as a first treatment for oxidate stress and inadequate blood flow to be followed by colloid or blood transfusion for volume replacement and oxygen delivery. This is a major departure or paradigm shift from this (JCH) and other inventors' past rationale, cited as prior art patents, for current hemoglobin based oxygen carriers (HBOCs), which was for HBOCs to serve as a temporary replacement of the "oxygen carrier" function of the red blood cells (RBCs). It is novel to create multifunctional HNPs that are NOT dependent on their oxygen caning capacity. In fact, in this invention, the oxygen binding is BLOCKED through carboxylation of the oxygen binding sites of HNPs' heme iron. The carboxylation also aids in the reduction of nitric oxide scavenging and adds anti-inflammatory activity. The earlier patents of one inventor (JCH) recognized the need to address oxidative stress BUT were still based on the concept of HBOCs as "oxygen carriers" as had been the prevalent rationale in the current generation HBOC development Proposal of therapeutic use of HNPs is novel and is contra indicated in the field of HBOC development, which still targets HBOC use as a temporary replacement of the oxygen carrying function of RBCs. The fact that even large volume HBOC use of up to the equivalent of 20 units of packed RBCs did not show therapeutic benefit would seem to doom any hope of FDA approval of an HBOC as an oxygen carrier. This invention is a fundamental revision of the concepts of how to increase the therapeutic index of HBOCs. It provides a means to address the toxicities of HBOCs related to their pro-oxidant activities brought about by moving the hemoglobin from the protective intra-RBC environment to an acellular vascular compartment. The novel concept of HNPs is to make them multifunctional therapeutics without regard to their initial oxygen carrier function by creating novel activities to maintain nitric oxide levels, remove reactive oxygen species (ROS), and correct inadequate blood flow.

Specifically the polynitroxylated pegylated carboxy hemoglobin (PNPH) is unique in that it is highly neuroprotective both in vivo and in vitro. The stability, configuration and synergy of carboxylation, pegylation and nitroxylation effects contribute to the unique therapeutic activities demonstrated in several animal models of un-met medical needs in transfusion and critical care medicine, which are described below.

The ability of the current generation HBOCs to transport oxygen has been well established (See U.S. Pat. Nos. 3,925,344, 4,001,200, 4,001,401, 4,053,590, 4,061,736, 4,136,093, 4,301,144, 4,336,248, 4,376,095, 4,377,512, 4,401,652, 4,473,494, 4,473,496, 4,600,531, 4,584,130, 4,857,636, 4,826,811, 4,911,929 and 5,061,688). However, the FDA/NIH Workshop entitled "HEMOGLOBIN BASED OXYGEN CARRIERS: CURRENT STATUS AND FUTURE DIRECTIONS", held in Bethesda, Md., Apr. 30, 2008 concluded that ALL HBOCs in advanced clinical trials have unacceptable cardiovascular mortality and morbidity (Also see Natanson C et al *JAMA* 2008; 299:2304) and that higher therapeutic index "next generation" HBOCs need to be developed. Therefore there is a major crisis and a roadblock in the development of next generation HBOCs. A next generation HBOC, which does not rely on its oxygen carrying activity to improve its therapeutic index is not obvious. In fact, the FDA decision not to include one of the inventors (JCH) as a presenter at the April 2008 Workshop is further proof of the non-obviousness of the use of polynitroxylated HBOCs to produce higher therapeutic index HBOCs to those skilled in the art (See U.S. Pat. Nos. 5,591,710, 5,789,376, 6,048,967, and 6,323,175).

Restoring the anti-oxidant enzyme activities such as superoxide dismutase (SOD) and catalase found in RBCs along with the oxygen carrying capacity of hemoglobin through co-polymerization and cross-linking to provide anti-inflammatory activities has been established (See U.S. Pat. No. 5,606,025). Likewise, the covalent labeling of multiple copies of a nitroxide to HBOCs to provide SOD and catalase mimetic activities has also been established (See U.S. Pat. Nos. 5,591,710, 5,789,376, 6,048,967, and 6,323,175). However, these current generation HBOCs have not yet reached advanced clinical trial stage in their development. Alternatively, by focusing on the correction of nitric oxide scavenging activities of the current generation HBOCs in advanced clinical trials, the use of nitrite and inhalation nitric oxide (iNO) has also been proposed (See U.S. Pat. Application Document Nos. 20070154569 and 20100051025)). Also, the use of nitrosated hemoglobin was proposed (See U.S. Pat. Nos. 6,627,738; 6,197,745; 6,884,773 and 6,911,427). However, it is still unknown as to whether these modifications of the current generation HBOCs will produce high therapeutic index next generation HBOCs acceptable to FDA.

Under the guidance from the FDA Workshop of 2008, the next generation HBOCs will have to prove to have a high therapeutic index and a novel mechanism of action in animal models of unmet medical needs in order to proceed into advanced clinical trials.

One of the current inventors (JCH) has issued patents on polynitroxylated hemoglobin (PNH) including U.S. Pat. Nos. 5,591,710, 5,789,376, 6,048,967, and 6,323,175. This inventor demonstrated that polynitroxylation "uniformly" transformed HBOCs into SOD and catalase mimetics, and advocated that this technology was a "universal" solution to provide anti-oxidative stress activities to current generation HBOCs This inventor stated in abandoned U.S. Pat. No. 6,458,758, "Compositions and processes to alleviate free radical toxicity are disclosed based on the use of nitroxides in association with physiologically compatible macromolecules. In particular, hemoglobin-based red cell substitutes are described featuring stable nitroxide free radicals for use in cell-free hemoglobin solutions, encapsulated hemoglobin solutions, stabilized hemoglobin solutions, polymerized hemoglobin solutions, conjugated hemoglobin solutions, nitroxide-labelled albumin, and nitroxide-labelled immunoglobulin. Formulations are described herein that interact with free radicals, acting as antioxidant enzyme-mimics, which preserve nitroxides in their active form in vivo. Applications are described including blood substitutes, radioprotective agents, imaging agents, agents to protect against ischemia and reperfusion injury, particularly in cerebral ischemia in stroke, and in vivo enzyme mimics among others". However, the inventors have proven beyond doubt that the claim that nitroxide alone would be sufficient to rescue the current generation HBOCs is without sufficient proof. In fact, as an example of the non-uniform effect of labeling of nitroxide alone, polynitroxylation of carboxy PolyHeme®, a polymerized hemoglobin produced by Northfield Laboratories, did not provide the anti-oxidant activities necessary to reduce vasoconstriction when tested by the method of Yu B., et al., 2010 (results not shown) nor did it reduce infarction in a MCAo stroke model using the method of Endres M., et al., 1997 (results not shown). The current invention by the co-inventors (JCH and LM) presents a major departure from the prior art in that only preferred compositions of pegylated carboxy hemoglobin when polynitroxylated have the requisite therapeutic index to meet the un-met medical needs in transfusion and critical care medicine.

The co-inventors discovered that focusing on the oxygen carrying and transport capacities of the HBOCs was a major flaw in the prior art. The co-inventors have provided further proof that focusing on only the preservation of nitric oxide levels through the removal of superoxide in combination with the reduction of hydrogen peroxide levels as in polynitroxylated albumin did not have sufficient therapeutic index in a TBI model (Exo J L., et al., 2009). The inventors also speculate that supplementation of nitric oxide via inhalation (iNO) (See US Patent Application Document n 20100051025) or through nitrite supplementation (See Patent Application Document ##20070154569) may not provide the therapeutic index to revive the current generation HBOCs in advanced clinical trials such as the polyhemoglobins from the now bankrupt companies of BioPure Corporation and Northfield Laboratories.

The inventors, however, propose that the redox coupling of the nitroxide in the polynitroxylated pegylated carboxy hemoglobin (PNPH) is a potential candidate for approval by FDA for un-met medical need in transfusion and critical care medicine. The inventors recognize that it is far more important for the PNPH to serve as a therapeutic to restore inadequate blood flow without reperfusion injury than to carry oxygen, which is a major departure from the focus of the prior art. Results with novel PNPH compositions will be presented to show that sustaining the mechanism of vascular patency even at very low concentrations of the PNPH is a key function to maintaining the balance of vascular nitric oxide and superoxide.

This invention represents a paradigm shift in transfusion and critical care medicine. The selection of a preferred embodiment of a novel neurovascular protective multifunctional PNPH, i.e. polynitroxylated pegylated bovine carboxy hemoglobin (bPNPH), as a resuscitative fluid to meet major un-met medical needs is discussed below:

1. Three animal models of un-met medical needs in transfusion and critical care medicine are used to evaluate the therapeutic efficacies and mechanisms of action of PNPH, namely:
    a) Traumatic brain injury (TBI) with or without hemorrhagic shock (HS) in the pre-hospital setting where blood is not available;
    b) Stroke therapy; and
    c) Sickle cell disease (SCD).
2. The preferred PNPH formulation was selected for its
    a) in vitro and in vivo neurovascular protective activities
    b) preservation of hemodyamic stability
    c) hyperoncontic activity, i.e. minimization of the volume required for resuscitation
    d) enhancement of cerebral oxygenation in TBI
    e) minimization of intracranial pressure increase in TBI
    f) lack of vasoconstriction in all three models
    g) maintenance of adequate blood flow to the penumbral region surrounding the ischemic core in stroke
    h) prevention or reduction of hemorrhage to expand the therapeutic window for thrombolytic tPA therapy in ischemic stroke
    i) correction of the aortic stiffness and pulmonary hypertension in chronic hemolytic oxidative stress in SCD model
    j) prevention or treatment of vaso-occlusive crisis from oxidative stress in SCD patients
    k) maximization of the synergistic effect of carboxylation, pegylation, and polynitroxylation
    l) maximization of the synergistic effect of hyperoximia and PNPH
3. The preferred PNPH formulation was selected to enhance the therapeutic index by taking advantage of the heme iron/nitroxide redox coupling within the hydrated shell of PNPH
4. The preferred PNPH formulation was selected to enhance the therapeutic index by taking advantage of the redox-coupling with endogenous anti-oxidants such as ascorbate
5. The PNPH oxygen carrying and release properties are of secondary importance compared to its therapeutic properties in complete contrast to current generation HBOCs.

Figures and Examples are included to illustrate these paradigm shifts and showcase the therapeutic potency and efficacy of PNPH resulting from a novel synergy of carboxylation, pegylation and polynitroxylation of redox coupled hemoglobins.

SUMMARY OF INVENTION

This invention relates to the discovery of a high therapeutic index polynitroxylated pegylated carboxy hemoglobin (PNPH). PNPH derives its therapeutic index from the synergy of the triple chemical modifications of carboxylation, pegylation, and polynitroxylation of a 64 Kd hemoglobin. PNPH overcomes the toxicity issues of current generation HBOCs as demonstrated in the therapeutic efficacies in disease models of transfusion and critical care medicine.

DETAILED DESCRIPTION

The following is a detailed description of the invention including methods of preparation and composition selection from 3 different compositions and 4 specific methods of uses in disease models of TBI+HS, stroke, SCD, and TBI+HS resuscitation with conjunctive use of 100% oxygen.

Methods of preparation of three (3) polynitroxylated pegylated carboxy hemoglobins and polynitroxylated carboxy PolyHeme:

(A) 250 ml of pegylated bovine hemoglobin (pegylated with 5 kDa polyethylene glycol) at 4% (40 g/L) hemoglobin protein supplied by Prolong Pharmaceuticals Inc. N.J. was first converted to carboxy pegylated hemoglobin under 15 psi of CO gas pressure in a sterile sealed glass container with mechanical stirring at 37° C. Then 4-(2-bromoacetamido)-2,2,6,6-tetramethyl-1-piperidinyloxyl (BrAcTPO), equivalent to 16 nitroxides per hemoglobin molecule, was added and pH was adjusted to 9.5. The reaction was permitted to proceed for 4.0 hours. At the termination of the reaction, the reaction mixture was first coarse filtered through a 0.4-micron filter followed with a 0.22-micron filter. The filtrate was then washed with 15 volumes of water-for-injection and concentrated to 4% (40 g/L) hemoglobin. The concentrated bPNPH was then 0.22-micron filtered and filled into a series of 50 ml transfusion bags pre-gamma irradiated to ensure sterility and stored at 4° C. before use. Positive CO pressure was used during entire procedure to ensure the final product was fully in its carboxy liganded state.

(B) Human stroma free carboxy hemoglobin was pegylated by reaction with 3 molar equivalents activated Pegmaleimide (MW 20 kD, purchased from SunBio, S. Korea) according to a modified published procedure (Cabrales P., et al., 2004). 250 ml of pegylated human carboxy hemoglobin at 4% (40 g/L) was then polynitroxylated under 15 psi of CO gas pressure in a sterile sealed glass container with mechanical stirring at 37° C. in the following manner. BrAcTPO, equivalent to 28 nitroxides per hemoglobin, was added and the pH was adjusted to 9.5. The reaction was permitted to proceed for 4.0 hours. At the termination of the reaction, the reaction mixture was first coarse filtered through a 0.4-micron filter followed with a 0.22-micron filter. The filtrate was then washed with 15 volumes of water-for-injection and concentrated to 4% hemoglobin. The concentrated hPNPH20 was then 0.22-micron filtered and filled into a series of 50 ml transfusion bags pre-gamma irradiated to ensure sterility and stored at 4° C. before use. Positive CO pressure was used during entire procedure to ensure the final product was fully in its carboxy liganded state.

(C) Human stroma free carboxy hemoglobin was pegylated by reaction with 15 molar equivalents activated Peg-maleimide (MW 5 kD, purchased from SunBio, S. Korea) according to a modified published procedure (Cabrales P., et al., 2004). 250 ml of pegylated human carboxy hemoglobin at 4% (40 g/L) was then polynitroxylated under 15 psi of CO gas pressure in a sterile sealed glass container with mechanical stirring at 37° C. in the following manner. BrAcTPO, equivalent to 18 nitroxides per hemoglobin, was added and the pH was adjusted to 9.5. The reaction was permitted to proceed for 4.0 hours. At the termination of the reaction, the reaction mixture was first coarse filtered through a 0.4-micron filter followed with a 0.22-micron filter. The filtrate was then washed with 15 volumes of water-for-injection and concentrated to 4% hemoglobin. The concentrated hPNPH05 was then 0.22-micron filtered and filled into a series of 50 ml transfusion bags pre-gamma irradiated to ensure sterility and stored at 4° C. before use. Positive CO pressure was used during entire procedure to ensure the final product was fully in its carboxy liganded state.

(D) Human Polyheme with a hemoglobin protein concentration of 12% (120 g/L) from Northfield Laboratories, Chicago, Ill., was first converted to carboxy Polyheme and then polynitroxylated under 15 psi of CO gas pressure in a sterile sealed glass container with mechanical stirring at 37° C. in the following manner. BrAcTPO, equivalent to 20 nitroxides per hemoglobin, was added and the pH was adjusted to 9.5. The reaction was permitted to proceed for 4.0 hours. At the termination of the reaction, the reaction mixture was first coarse filtered with a 0.4-micron filter followed with a 0.22-micron filter. The filtrate was then washed with 15 volumes of water-for-injection and concentrated to 4% (40 g/L) hemoglobin. The concentrated polynitroxylated carboxy Polyheme was then 0.22-micron filtered and filled into a series of 50 ml transfusion bags pre-gamma irradiated to ensure sterility and stored at 4° C. before use. Positive CO pressure was used during entire procedure to ensure the final product was fully in its carboxy liganded state.

Figure 1:
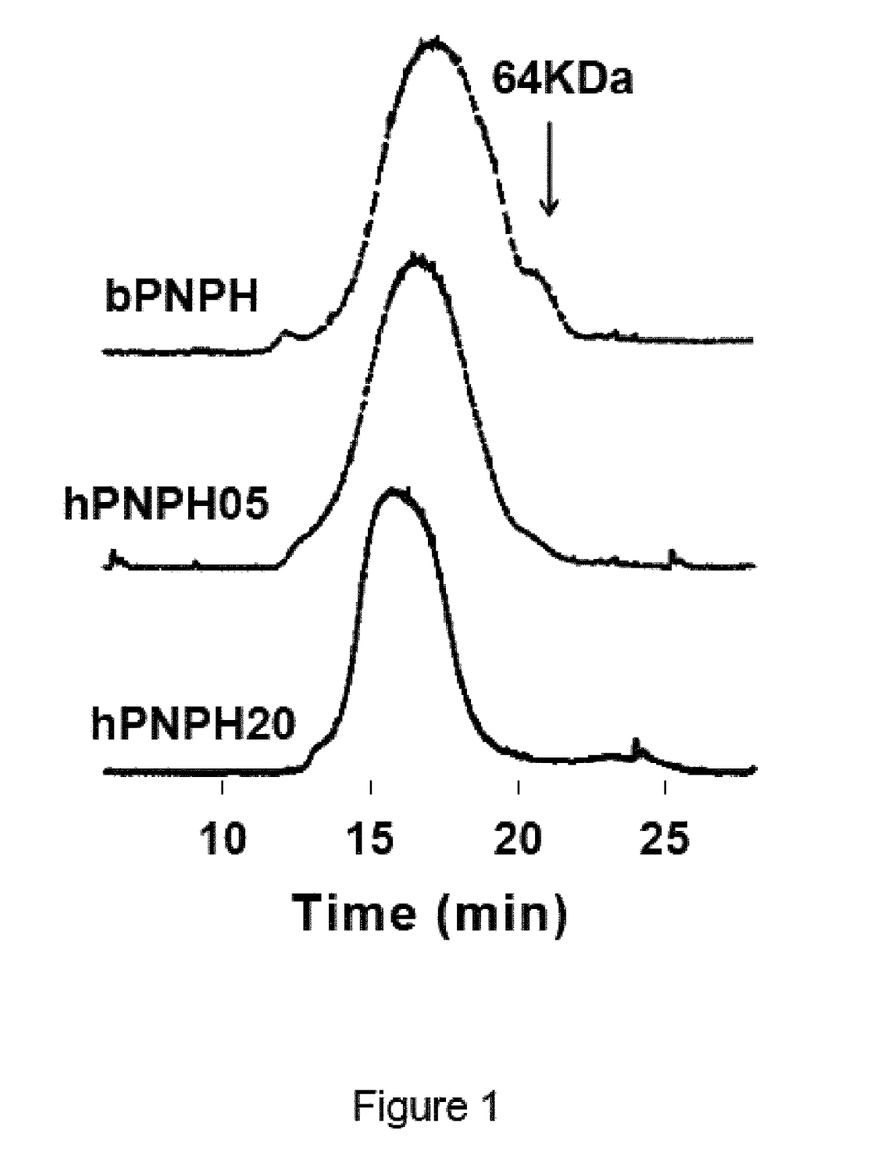
FIG. 1. Molecular size distributions of polynitroxylated pegylated (5 KDa) bovine carboxy hemoglobin (bPNPH), polynitroxylated pegylated (5 KDa) human carboxy hemoglobin (hPNPH05), and polynitroxylated pegylated (20 KDa) human carboxy hemoglobin (hPNPH20) measured by FPLC. Experimental conditions: Superose 12 column with 50 mM phosphate buffered saline (pH=7.4) at a flow rate of 30 ml/hr.

Efficacy of polynitroxylation: The nitroxide to hemoglobin ratio determined by electron paramagnetic resonance spectroscopy of the polynitroxylated pegylated carboxy hemoglobins is approximately 12 for bPNPH, 24 for hPNPH20 and 14 for hPNPH05 and 10 for polynitroxylated carboxy Polyheme. The molecular weight analyses of the bPNPH, hPNPH20 and hPNPH05 by FPLC post polynitroxylation are shown in FIG. 1. These PNPH preparations are essentially free of un-pegylated hemoglobin. FPLC elution profile of polynitroxylated carboxy Polyheme was essentially unaltered by polynitroxylation (Result not shown).

Figure 2:
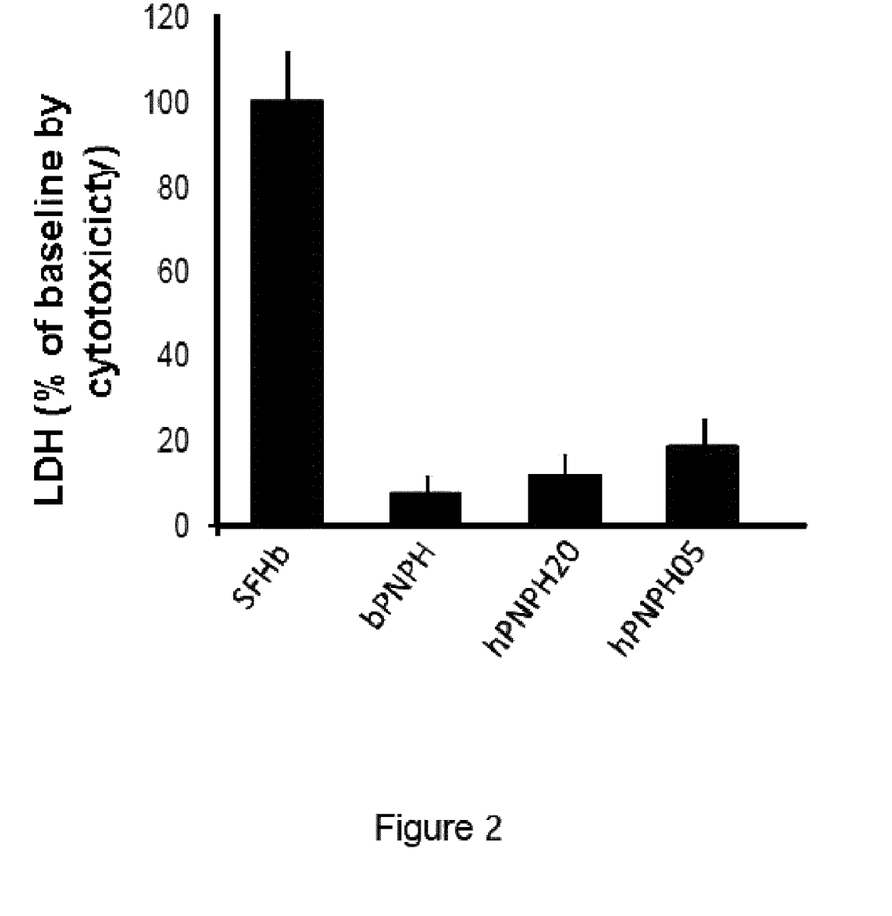
FIG. 2. Cytotoxicity of free carboxy hemoglobin (SFHb), polynitroxylated pegylated (5 KDa) bovine carboxy hemoglobin (bPNPH), polynitroxylated pegylated (20 KDa) human carboxy hemoglobin (hPNPH20), and polynitroxylated pegylated (5 KDa) human carboxy hemoglobin (hPNPH05) in primary rat cortical neurons assayed by lactate dehydrogenase (LDH) release, an indicator of neuronal cell injury, at 24 hours with 15 μM tetramer equivalent hemoglobin. Data are expressed at mean+/−SD, n=3.

In Vitro Neuroprotective Properties of Polynitroxylated Pegylated Carboxy Hemoglobins FIG. 2 shows the difference in the in vitro neuroprotective activities of the three (3) PNPH preparations as well as bovine stroma free hemoglobin (used as control). All test and control preparations were at 4% (40 g/L) hemoglobin. The neuroprotective potency order is bPNPH>hPNPH20>hPNPH05.

It appears that the neuroprotective activities of the PNPHs are not directly correlated to their nitroxide to hemoglobin ratio, i.e. hPNPH20 with 24 nitroxides per hemoglobin was less effective than bPNPH with 12 nitroxides per hemoglobin. Bovine stroma free hemoglobin is neurotoxic while the bPNPH appears to be the most neuroprotective. The remaining two PNPHs also appear to be neuroprotective but are somewhat less potent (See FIG. 2).

Figure 3:
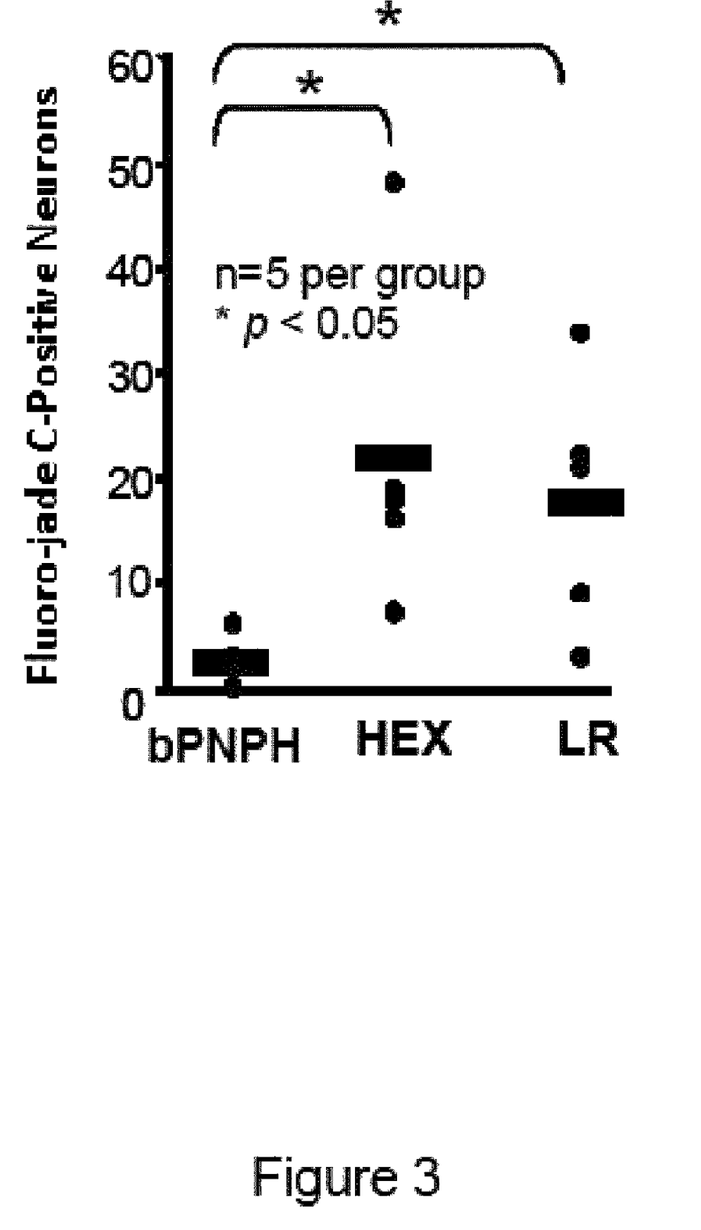
FIG. 3. Neurodegeneration, assessed via Fluoro-jade C staining to detect dead or dying cells, in CA 1 hippocampus ipsilateral to the injury at 7 days post injury in a mouse model of traumatic brain injury (TBI) complicated with hemorrhagic shock (HS) showing the comparative in viva neuroprotective activities of bPNPH and a standard crystalloid (Lactated Ringer (LR), standard for civilian resuscitation), and a standard colloid (Hextend (HEX), standard for military resuscitation).

In Vivo Neuroprotective Properties of the Bovine Polynitroxylated Pegylated Carboxy Hemoglobin FIG. 3 shows the in vivo neuroprotective activities of bPNPH against a standard crystalloid (Lactated Ringer (LR), standard for civilian resuscitation) and a standard colloid (Hextend (HEX), standard for military resuscitation) in a mouse model of traumatic brain injury (TBI) complicated with hemorrhagic shock (HS) simulating the pre-hospital patient care according to a published method (Dennis A M, et al., 2009). According to this model the mouse first received a TBI followed by 90 min of HS with hypotensive resuscitation and then re-infusion of shed blood 120 min post resuscitation. Histology and histological staining on surviving mice performed 7 days after brain injury was used to determine neuroprotection. It is clear that bPNPH provided the most neuroprotection as compared to the 2 standard pre-hospital resuscitative fluids.

Figure 4:
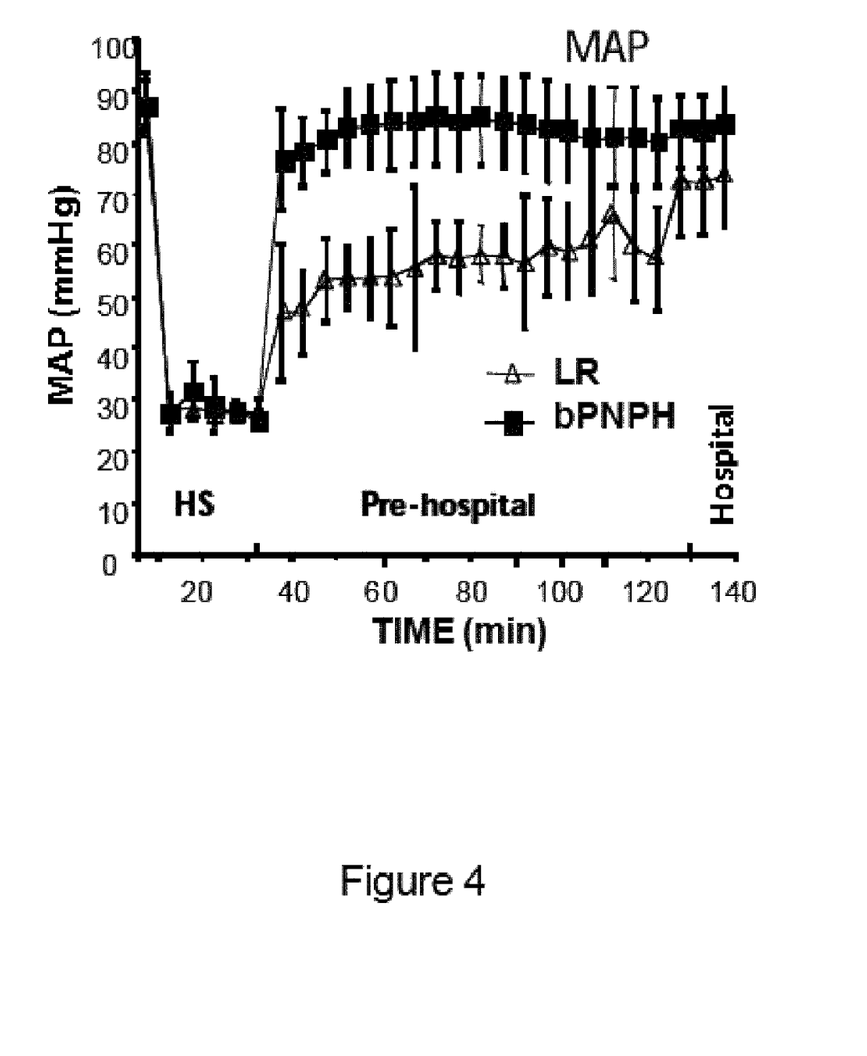
FIG. 4. The hemodyamic properties of bPNPH vs Lactated Ringers (LR) in a mouse model of TBI+HS. In a hypotensive resuscitation strategy for TBI+HS to control bleeding, PNPH clearly showed superiority to LR in mean arterial pressure (MAP) restoration and stability in a pre-hospital setting.

Hemodynamic Properties of the Bovine Polynitroxylated Pegylated Carboxy Hemoglobin in Mouse Model of TbI+HS FIG. 4 shows the hemodyamic properties of bPNPH vs Lactated Ringers (LR) in a mouse model of TBI+HS. In a hypotensive resuscitation strategy for TBI+HS to control bleeding, bPNPH clearly showed superiority to LR in mean arterial pressure (MAP) restoration and stability.

The volume required for resuscitation (restoration of mean arterial pressure) with the bovine polynitroxylated pegylated carboxy hemoglobin in a mouse model of TBI+HS is only 18% or 64% of the volume required for resuscitation with Lactated Ringers (LR) or Hextend (HEX), respectively (results not shown). When expressed in volume per kilogram dose, bPNPH, HEX, and LR treated groups required 6.7-±1.8 ml/kg, 9.6-±2.6 ml/kg, and 36.3±11.5 ml/kg, respectively. The smaller volume requirement with bPNPH would make it much easier to have therapeutic quantities available in a pre-hospital setting as well as in field use for combat casualty care. However, more importantly, the smaller infusion volume would reduce edema of the brain, which is an even more important therapeutic benefit for TBI treatment in a pre-hospital setting.

Figure 5:
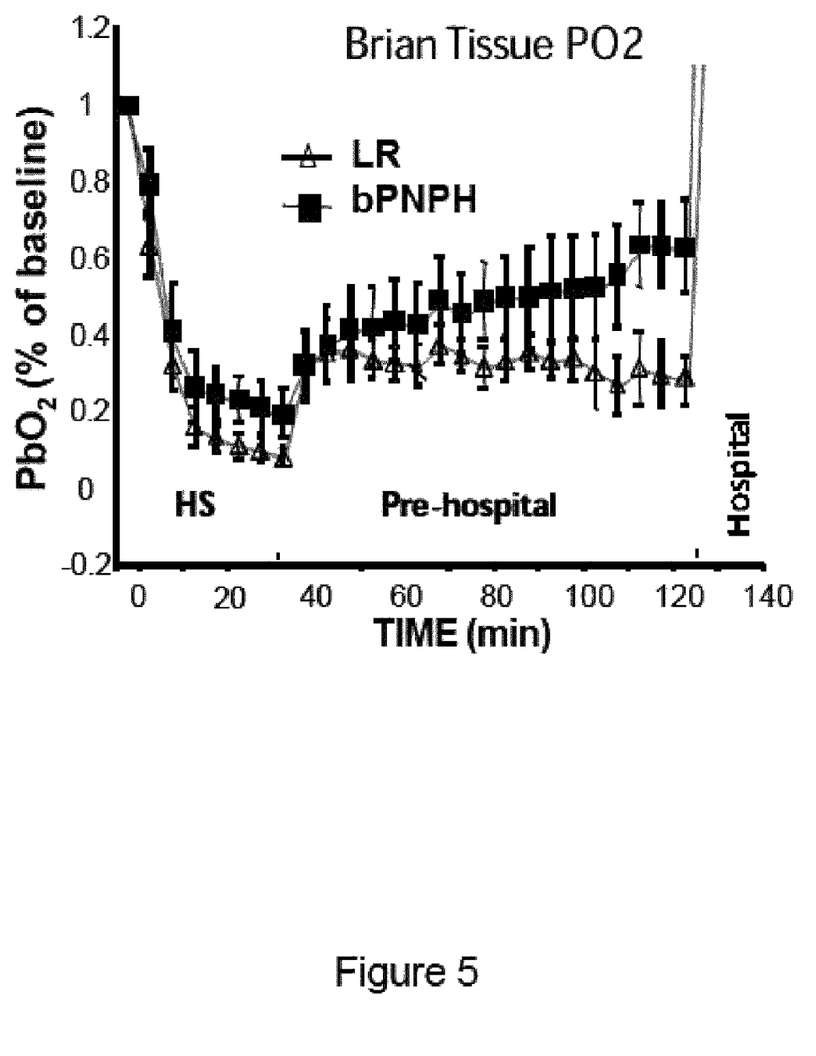
FIG. 5. The direct measurement of the brain tissue oxygenation immediately below the impact by implanted oxygen electrode after TBI impact. It is clear that bPNPH maintains the cerebral oxygen levels much better than Lactated Ringers (LR).

Cerebral Oxygenation with the Bovine Polynitroxylated Pegylated Carboxy Hemoglobin in Mouse Model of TbI+HS FIG. 5 shows the direct measurement of the brain tissue oxygenation after TBI impact immediately below the TBI impact as measured by an implanted oxygen electrode. It is clear that bPNPH maintains the cerebral oxygen levels much better than Lactated Ringers. This beneficial effect is most pronounced 2 hours post TBI. Therefore the bPNPH appears to have a long lasting effect in maintaining cerebral blood flow and tissue oxygenation. This is truly a remarkable finding which supports the histological finding of neurological-tissue protection shown in FIG. 3 above.

Figure 6:
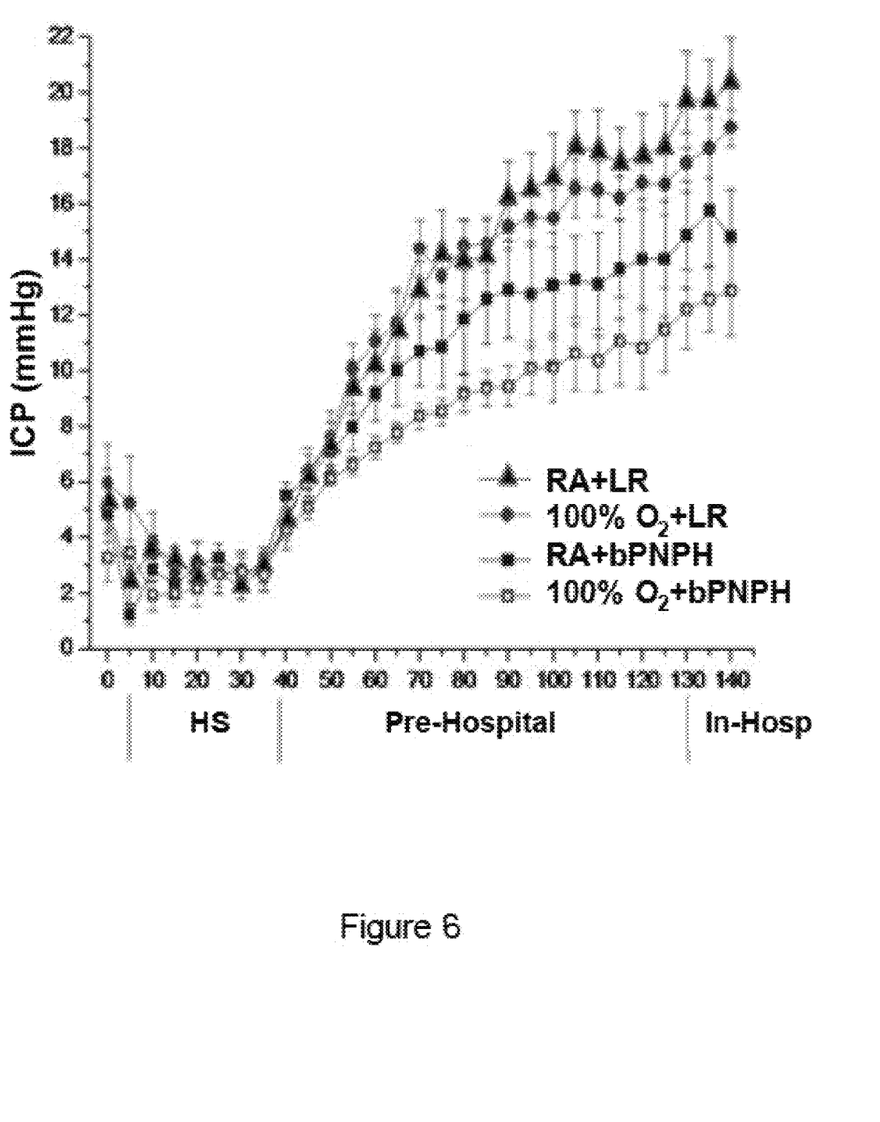
FIG. 6. The rate and extent of intracranial pressure (ICP) increase, which is significantly reduced in bPNPH treated animals as compared to that of the Lactated Ringers (LR) resuscitated animals both with room air (RA) resuscitation or with conjunctive inhalation of 100% oxygen in a pre-hospital setting.

Intra Cranial Pressure (ICP) Reduction by the Bovine Polynitroxylated Pegylated Carboxy Hemoglobin in Mouse Model of TBI+HS FIG. 6 shows that the rate and extent of ICP increase is significantly reduced in bPNPH treated animals as compared to that of the Lactated Ringers resuscitated animals. This result indicates that there is less brain swelling and edema in this TBI+HS model. This is a highly significant benefit of bPNPH in pre-hospital resuscitation as this treatment adds valuable time for evacuation during the golden hour for the patient to reach the hospital in time for definitive surgical treatment to relieve ICP.

Intra Cranial Pressure (ICP) Reduction with Conjunctive use of 100% Oxygen and the Bovine Polynitroxylated Pegylated Carboxy Hemoglobin in Mouse Model of TBI+HS FIG. 6 also shows that the rate and extent of ICP increase is significantly reduced in bPNPH treated animals and can be further reduced with conjunctive inhalation of 100% oxygen in the pre-hospital setting. This result is highly significant based on the increased mortality of pre-hospital use of 100% oxygen (JAMA clinical trial report 2010). Kilgannon J H, et al., reported in June issue of JAMA in 2010 that patients who have excessive oxygen levels in arterial blood (hyperoxia) following resuscitation from cardiac arrest have a higher rate of death in the hospital than similar patients without arterial hyperoxia. This may be a highly significant benefit of PNPH when used in conjunction with 100% oxygen in pre-hospital resuscitation. We hypothesize that there is a potential synergy of combined use of PNPH with oxygen in a pre-hospital setting.

PNPH for Infarct Reduction in a Rat MCAo Model of Ischemic Stroke

Figure 7:
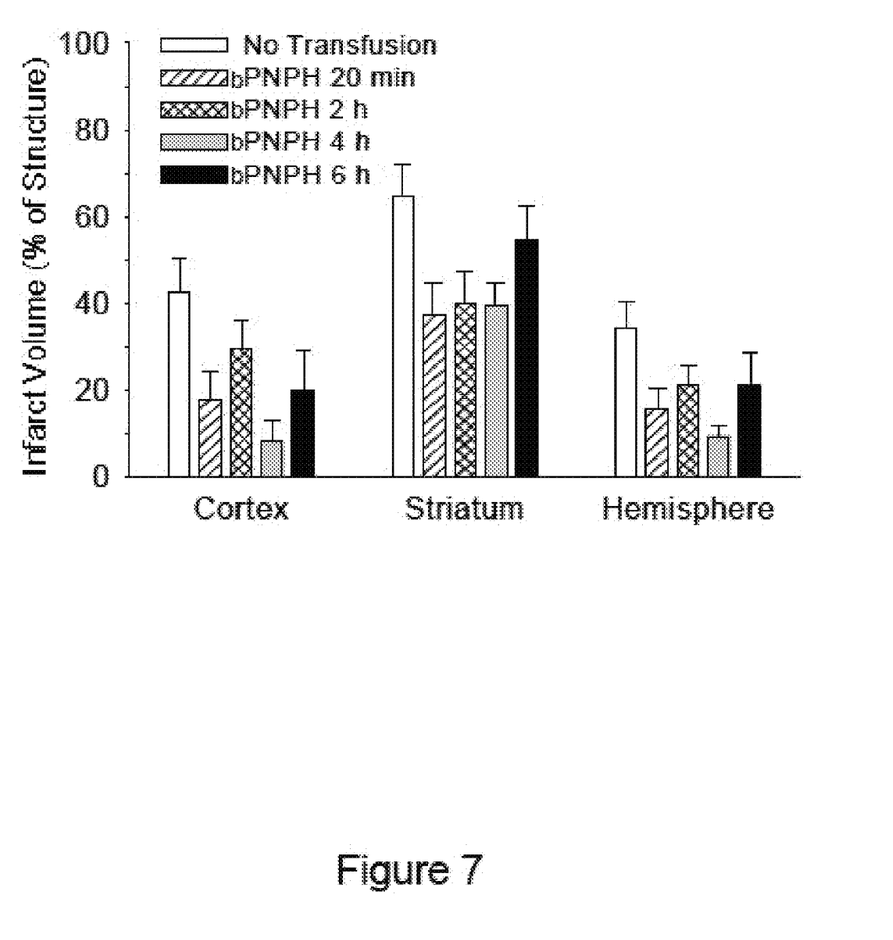
FIG. 7. Infarct volume (±SE) in cerebral cortex, striatum, and entire hemisphere after 2 hours (h) of middle cerebral artery occlusion (MCAo) with the intraluminal filament model and 3 days of reperfusion in rats with no transfusion (n=10) or with 10 ml/kg bPNPH transfusion at 20 min (n=11), 2 h (n=10), 4 h (n=8), or 6 h (n=9) after MCAo.

FIG. 7 shows infarct reduction with bPNPH resuscitation in transient MCAo model of ischemic stroke in rat. The neuroprotection is significant 4-6 hours post bPNPH transfusion. Based on these neuroprotective properties of bPNPH, it is hypothesized that PNPH may be used to treat both ischemic and hemorrhagic stroke in a pre-hospital setting.

Figure 8:
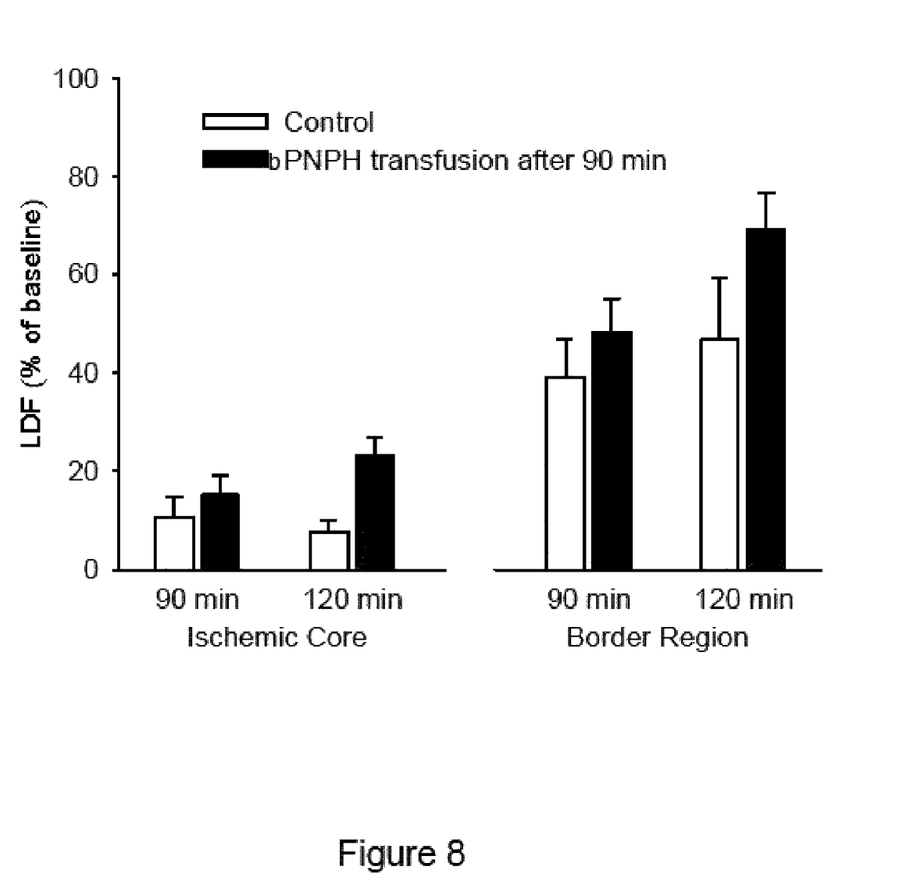
FIG. 8. Percent change from pre-ischemic baseline of Laser-Doppler flow (LDF) (±SE) at 90 min of MCAo (before transfusion) with the intraluminal filament technique and at 120 min of MCAo in rats with no transfusion (n=9) or with subsequent topload transfusion (10 ml/kg) of PNPH (n=7). PNPH improved blood flow in the ischemic border region with only a minor increase in MAP from 100±3 to 105±4 mmHg.

FIG. 8 shows that one mechanism of action of bPNPH in stroke infarct reduction is promotion of the blood flow in both the ischemic core and the border region. We hypothesize that bPNPH may also have the potential therapeutic benefit of extending the therapeutic window of delayed tPA treatment of ischemic stroke to up to 6 hours.

PNPH for the Reduction of Vascular Dysfunction in SCD

Figure 9:
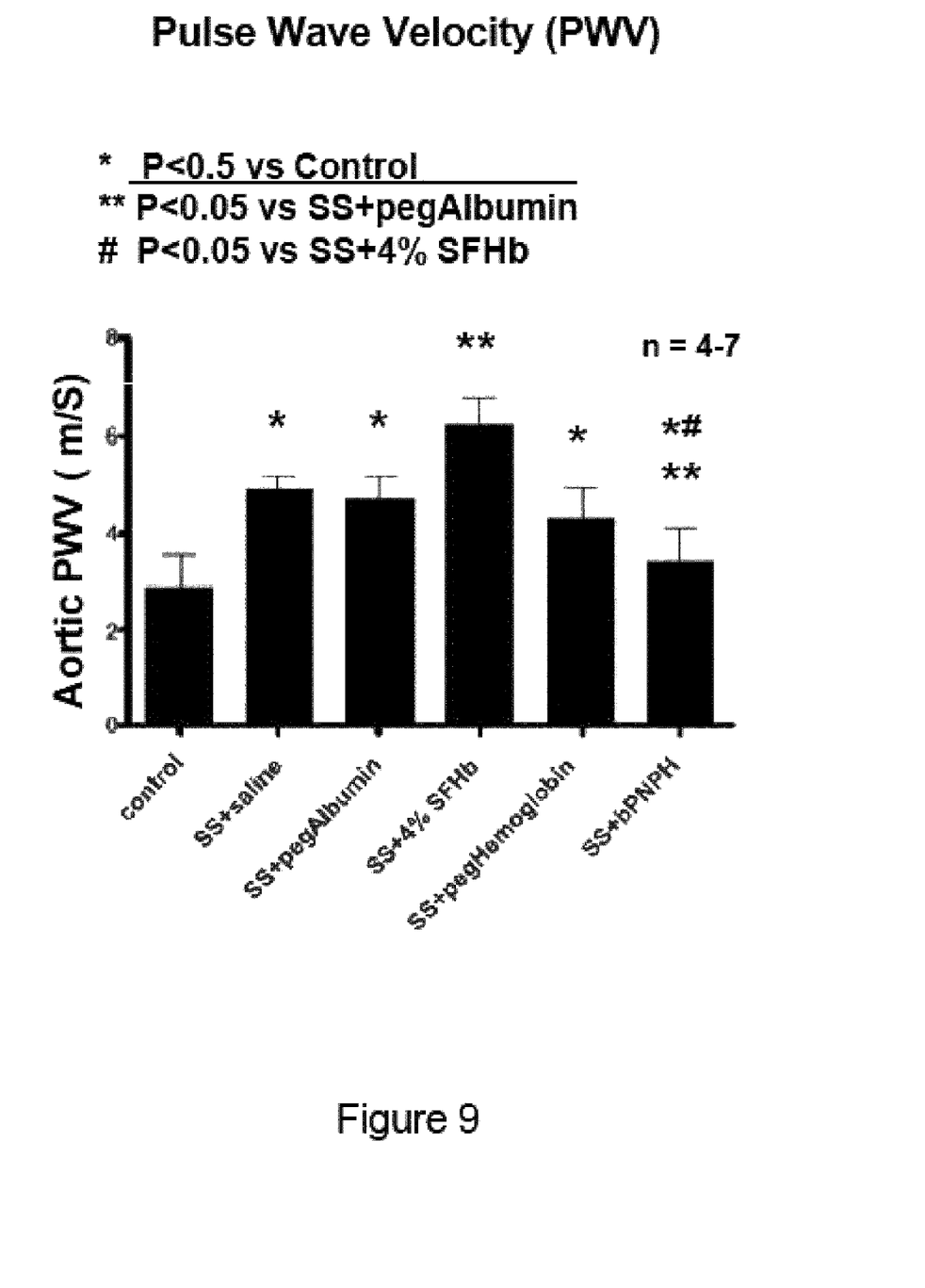
FIG. 9. Pulse wave velocity (PWV) for pulmonary vascular tone measured in meters per second (m/S) by invasive hemodynamic techniques in intact wild type (Control) and sickle cell mice (SS) infused with saline (SS+Saline), pegylated albumin (SS+pegAlbumin), 4% free hemoglobin (SS+SFHb), pegylated bovine carboxy hemoglobin (SS+pegHemoglobin), or polynitroxylated pegylated carboxy bovine hemoglobin (SS+bPNPH).

FIG. 9 shows that in a transgenic SCD mouse model the aortic stiffness resulting from global nitric oxide induced vascular dysfunction is reduced with bPNPH treatment In transgenic SCD mice, a top loading infusion of bPNPH equivalent to 1-2 units of packed RBCs appears to correct the nitric oxide dysfunction manifested as aortic stiffness as measured by pulse wave velocity (PWV). PegHb and other controls had no significant effects on PWV. We hypothesize that infusion of bPNPH may significantly correct the nitric oxide induced vascular dysfunction in SCD patients. bPNPH infusion in place of RBC transfusion may also reduce the oxidative stress from chronic hemolytic anemia. In conjunction with current use of hydroxylurea treatment bPNPH transfusion may result in the reduction or even elimination of allogenic blood transfusion for SCD patients.

Figure 10:
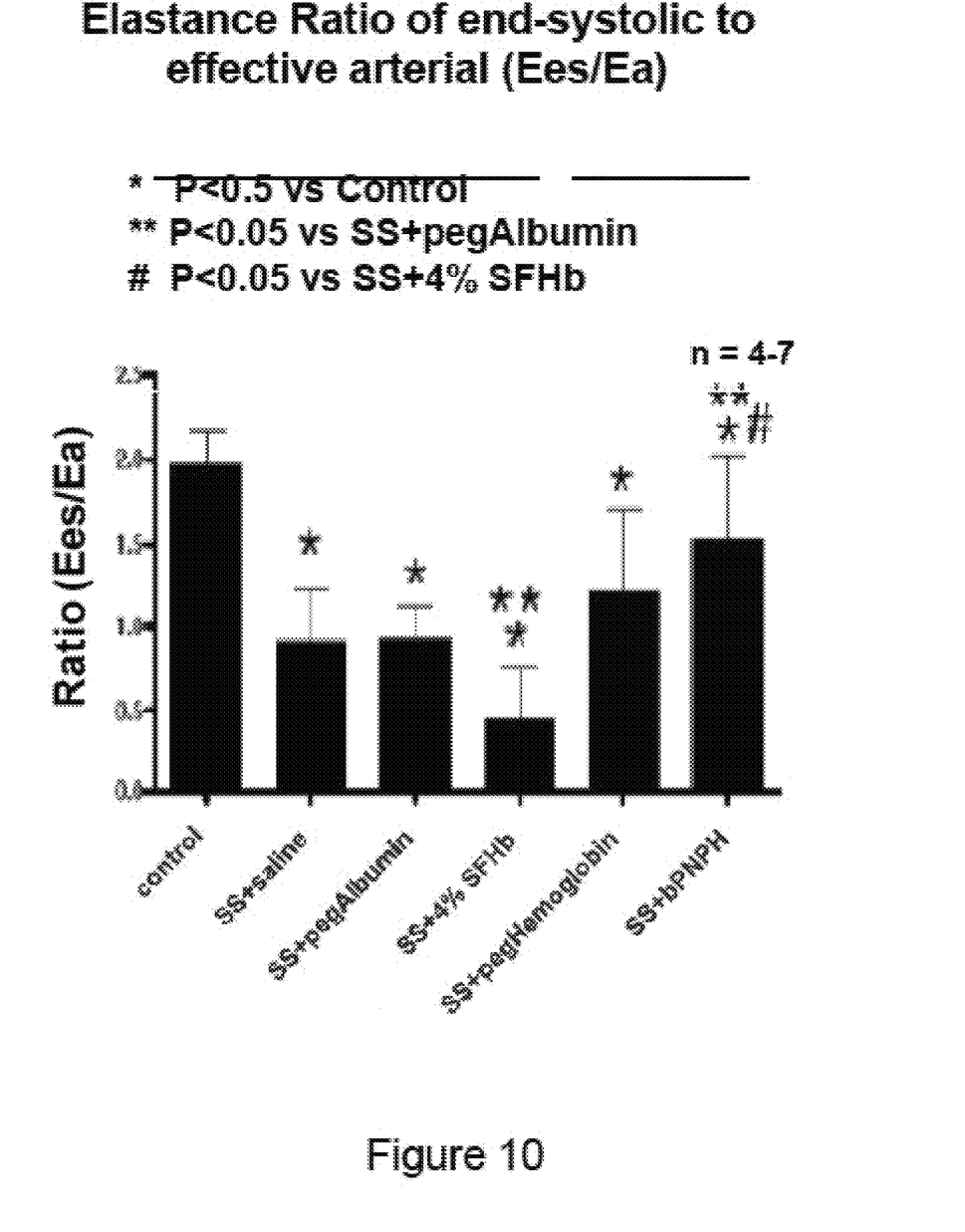
FIG. 10. End systolic elastance normalized for effective arterial elastance (Ees/Ea) for right ventricular-pulmonary vascular coupling measured by invasive hemodynamic techniques in intact wild type (Control) and sickle cell mice (SS) infused with saline (SS+Saline), pegylated albumin (SS+pegAlbumin), 4% free hemoglobin (SS+SFHb), pegylated bovine carboxy hemoglobin (SS+pegHemoglobin), or polynitroxylated pegylated bovine carboxy hemoglobin (SS+bPNPH).

Pulmonary hypertension is a highly prevalent complication of SCD and is a strong risk factor for early mortality. Hsu et al published their results in Blood in 2007 showing that in transgenic SCD mice chronic hemolytic anemia is sufficient to produce pulmonary hypertension. FIG. 10 shows that the chronic pulmonary hypertension induced by chronic hemolysis in transgenic sickle mice is reversed by bPNPH transfusion and is aggravated by control stroma free hemoglobin transfusion. This result in a model of SCD is significant in that the chronic vascular dysfunction of SCD may be treatable by bPNPH transfusion. This therapeutic efficacy may open the possibility of demonstrating bPNPH as a novel transfusion therapy in sickle cell disease.

Figure 11:
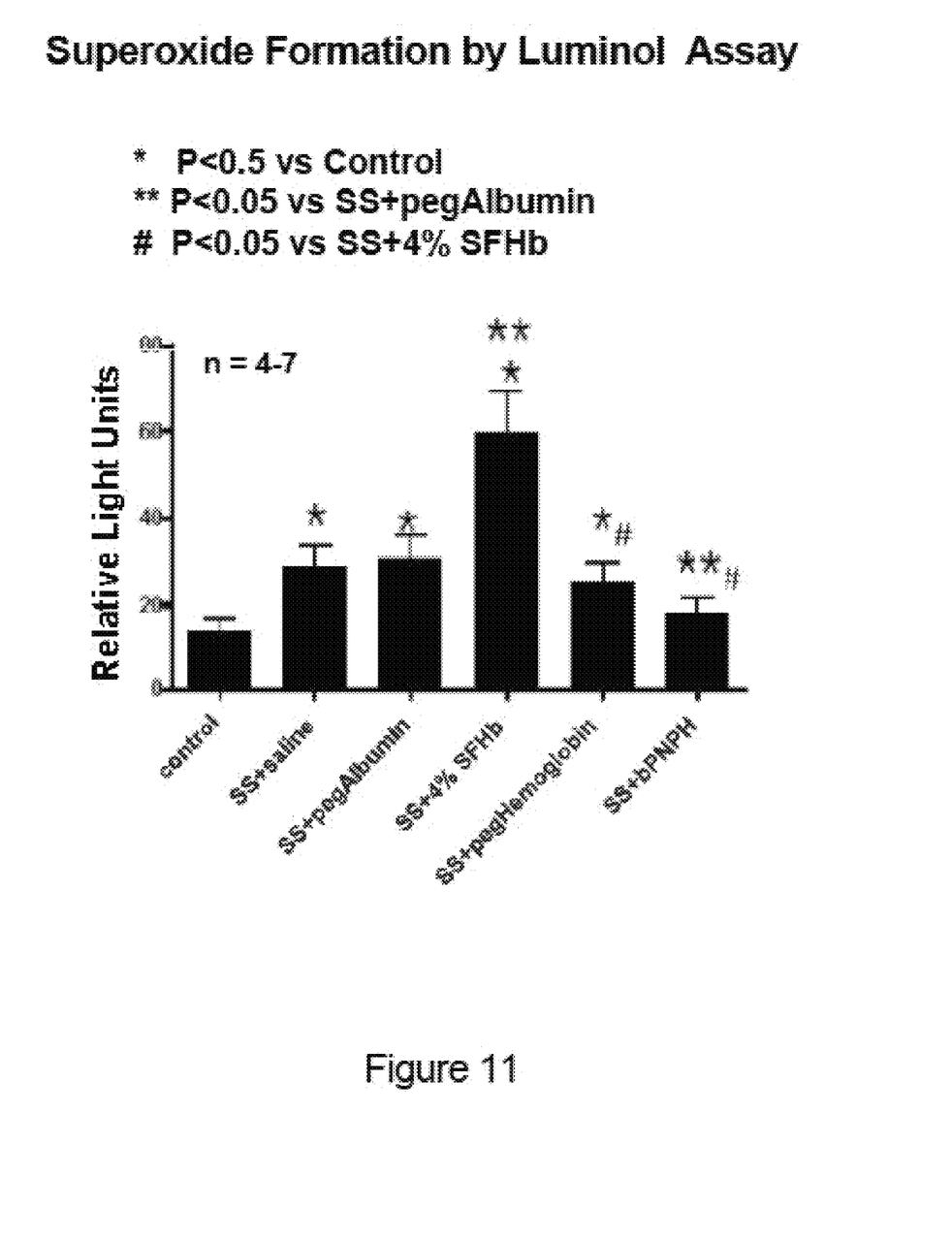
FIG. 11. Superoxide formation measured as relative light units (RLU) by luminol activity assays (luminol fluoresces in the presence of superoxide) in lung samples in intact wild type (Control) and sickle cell mice (SS) infused with saline (SS+Saline), pegylated albumin (SS+pegAlbumin), 4% free hemoglobin (SS+SFHb), pegylated bovine carboxy hemoglobin (SS+pegHemoglobin), or polynitroxylated pegylated bovine carboxy hemoglobin (SS+bPNPH).
Figure 12:
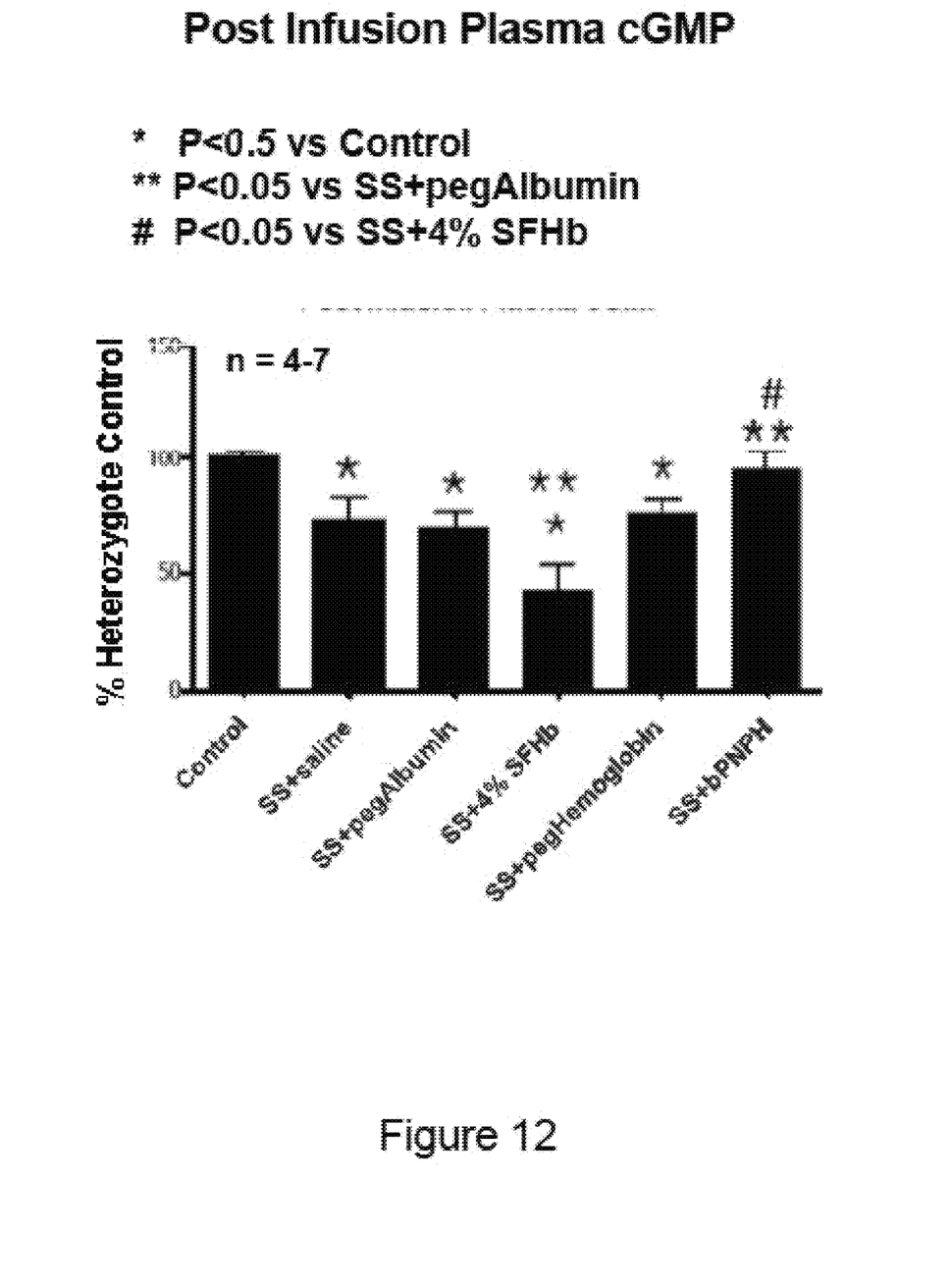
FIG. 12. Plasma cGMP (downstream effector of nitric oxide and natriuretic peptide activity) as measure of plasma nitric oxide levels in plasma of intact wild type (Control) and sickle cell mice (SS) infused with saline (SS+Saline), pegylated albumin (SS+pegAlbumin), 4% free hemoglobin (SS+SFHb), pegylated bovine carboxy hemoglobin (SS+pegHemoglobin), or polynitroxylated pegylated bovine carboxy hemoglobin (SS+bPNPH).

Preoperative transfusions are frequently given to prevent perioperative morbidity in patients with sickle cell anemia. In 1995, Vichinsky E P et al reported that a conservative transfusion regimen was as effective as an aggressive regimen in preventing perioperative complications in patients with sickle cell anemia, and the conservative approach resulted in only half as many transfusion-associated complications. The transfusion-associated complications are often caused by oxidative stress such as over production of vascular superoxide, which can be simulated with elevated stroma free hemoglobin level in transgenic mice. FIG. 11 shows that infusion of bPNPH simulating perioperative transfusion is capable of reducing the chronically high plasma superoxide levels in transgenic sickle mice to nearly that of their heterozygous littermate controls. This is further demonstration that a therapeutic mechanism of bPNPH is via reduction of superoxide, which in turn enhances plasma nitric oxide levels. We speculate that the potential to reduce perioperative complication would also be reflected by normalization of plasma nitric oxide levels as a result of bPNPH transfusion. FIG. 12 shows the restoration of plasma nitric oxide levels as a result of bPNPH transfusion as measured by downstream cGMP levels. This is further demonstration of the therapeutic mechanism of bPNPH in SCD.

Taken together, the results for this invention, shown in FIGS. 2-12, clearly demonstrate that bPNPH functions as a high therapeutic index, multifunctional agent that has the potential to treat specific diseases with oxidative stress such as SCD, stroke, and traumatic brain injury. These are likely the therapeutic efficacies required by FDA for a potential next generation HBOC. What is novel in this invention is that the NPHs, such as bPNPH, do not require the oxygen carrier as the essential therapeutic function. To the inventors this represents a major shift in the treatment paradigm in transfusion and critical care medicine.

The Disclosure of Examples of Preferred Compositions and Methods of their Use does not Limit this Invention to the Claims Below

REFERENCES

FDA/NIH Workshop "HEMOGLOBIN BASED OXYGEN CARRIERS: CURRENT STATUS AND FUTURE DIRECTIONS", Bethesda, Md., Wednesday, Apr. 30, 2008.

Natanson C., et al., Cell-free hemoglobin-based blood substitutes and risk of myocardial infarction and death: a meta-analysis. JAMA 299:2304-2312, 2008.

Yu B., et al., Endothelial dysfunction enhances vasoconstriction due to scavenging of nitric oxide by a hemoglobin-based oxygen carrier. Anesthesiology March; 112(3):586-94, 2010.

Dennis A M., et al., Hemorrhagic Shock after Experimental Traumatic Brain Injury in Mice: Effect on Neuronal Death. J Neurotrauma June, 26(6) 889-899, 2009.

Cabrales P., et al., Microvascular PO 2 during extreme hemodilution with hemoglobin site specifically PEGylated at Cys-93(beta) in hamster window chamber. Am J Physiol Heart Circ Physiol 287: H1609-H1617, 2004.

Exo J L., et al., Resuscitation of traumatic brain injury and hemorrhagic shock with polynitroxylated albumin, hextend, hypertonic saline, and lactated Ringer's: Effects on acute hemodynamics, survival, and neuronal death in mice. J. Neurotrauma 26(12):2403-8, 2009.

Kilgannon J H., et al., Excess oxygen in blood after cardiac resuscitation may increase risk of in-hospital death. *JAMA*. 303[21]: 2165-2171, 2010.

Hsu L L, et al., Hemolysis in sickle cell mice causes pulmonary hypertension due to global impairment in nitric oxide bioavailability. Blood 109(7): 3088-3098, 2007.

Vichinsky E P., et al., A comparison of conservative and aggressive transfusion regimens in the perioperative management of sickle cell disease. The Preoperative Transfusion in Sickle Cell Disease Study Group. N Eng J Med. 333(4): 206-13, 1995.

We claim:

1. Intravenous compositions of neurovascular protective multifunctional polynitroxylated pegylated carboxy hemoglobin (PNPH) comprising: a pegylated carboxy hemoglobin with covalently bound nitroxides in a physiologically compatible solution.

2. The PNPH of claim 1 wherein the hemoglobin is mammalian hemoglobin.

3. The PNPH of claim 1 or 2 wherein the core hemoglobin is either free-associating or intra sub-unit cross-linked.

4. The PNPH of claim 1 wherein the molecular weights of the covalently bound polyethylene glycol chains range from 5 kilo Dalton to 20 kilo Dalton.

5. The PNPH of claim 1 wherein the number of polyethylene glycol chains per hemoglobin molecule ranges from 2 to 10 with the lower numbers of polyethylene glycol chains associated with higher molecular weight polyethylene glycol chains and visa versa.

6. The PNPH of claim 1 is formulated for the resuscitation of traumatic brain injury with or without hemorrhagic shock.

7. The PNPH of claim 1 is formulated to replace red blood cell transfusion in pre-surgical blood transfusion in sickle cell disease patients to reduce the incidents of vaso-occlusive crisis.

8. The PNPH of claim 1 is formulated to reduce brain infarction in both hemorrhagic and ischemic stroke when used as the first treatment in a pre-hospital setting.

9. The PNPH of claim 1 is formulated to reduce brain infraction and hemorrhagic transformation in ischemic stroke patients and to extend the therapeutic window of thrombolytic agents such as recombinant tissue plasminogen activator (rtPA) and its analogues.

10. The PNPH of claim 1 is formulated to reduce brain swelling in traumatic brain injury, hemorrhagic and ischemic stroke when used as the first treatment in a pre-hospital setting.

11. The PNPH of claim 1 is formulated to reduce hyperoxic oxygen brain injury in cardiopulmonary resuscitation using 100% oxygen.

12. The PNPH of claim 1 is formulated to reduce hyperoxic oxygen brain injury in neonates as a pretreatment to oxygen treatment in an in-hospital setting.

13. The PNPH of claim 1 is formulated to reduce mortalities and morbidities from transfusion of red blood cells subjected to prolonged storage when PNPH is used as a conjunctive pretreatment or substitute treatment in an in-hospital setting.

14. The PNPH of claim 1 wherein the PNPH is prepared by two processes comprised of 1) Pegylation under nitrogen atmosphere and 2) polynitroxylation under carbon monoxide atmosphere.

15. The PNPH of claim 1 wherein the nitroxides are 2,2,6, 6-tetramethyl-1-piperidine-N-oxyl free radicals.

* * * * *